United States Patent
Yu

(10) Patent No.: US 9,910,165 B2
(45) Date of Patent: Mar. 6, 2018

(54) DETECTOR SYSTEM OF CT SCANNER

(71) Applicant: SHENYANG NEUSOFT MEDICAL SYSTEMS CO., LTD., Shenyang (CN)

(72) Inventor: Jun Yu, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 57 days.

(21) Appl. No.: 14/965,836

(22) Filed: Dec. 10, 2015

(65) Prior Publication Data

US 2016/0170038 A1 Jun. 16, 2016

(30) Foreign Application Priority Data

Dec. 12, 2014 (CN) .......................... 2014 1 0765565
Dec. 4, 2015 (CN) .......................... 2015 1 0889368

(51) Int. Cl.
*G01J 1/42* (2006.01)
*G01T 1/17* (2006.01)
(Continued)

(52) U.S. Cl.
CPC ................ *G01T 1/17* (2013.01); *A61B 6/032* (2013.01); *A61B 6/4085* (2013.01);
(Continued)

(58) Field of Classification Search
CPC ... A61B 6/4411; A61B 6/4291; A61B 6/4429; A61B 6/4452
See application file for complete search history.

(56) References Cited

U.S. PATENT DOCUMENTS 4,717,948 A * 1/1988 Sakai .................... H01L 21/565
257/786
5,998,867 A * 12/1999 Jensen ................ H01L 23/3135
174/104
(Continued)

FOREIGN PATENT DOCUMENTS

CN 1625320 A 6/2005
CN 101266297 A 9/2008
(Continued)

OTHER PUBLICATIONS

State Intellectual Property Office of the People's Republic of China, Office Action and Search Report Issued in Application No. 201510889368.2, dated Nov. 16, 2017, 12 pages. (Submitted with Partial Translation).

*Primary Examiner* — Kenneth J Malkowski
(74) *Attorney, Agent, or Firm* — McCoy Russell LLP

(57) ABSTRACT

A detector system for a CT scanner is provided. The detector system may include a plurality of detector modules. Each of the detector modules may include a supporting frame, two or more detectors and an interface board. A supporting frame may be connected to a casing of the detector system. Detectors may be mounted onto a supporting frame and may convert an X-ray beam within a CT scanner into an electrical signal. An interface board may be disposed in an outer side of a supporting frame away from the focus of an X-ray tube, and may be electrically connected to a plurality of detectors through a connector, so as to provide a control signal and a power supply to the detectors, and to transmit a digital signal outputted by the detectors to a backplane of the detector system through an output line.

12 Claims, 3 Drawing Sheets

(51) Int. Cl.
*G01T 7/00* (2006.01)
*G01T 1/29* (2006.01)
*A61B 6/03* (2006.01)
*A61B 6/00* (2006.01)

(52) U.S. Cl.
CPC .......... *A61B 6/4233* (2013.01); *G01T 1/2985* (2013.01); *G01T 7/00* (2013.01)

(56) References Cited

U.S. PATENT DOCUMENTS

| | | | |
|---|---|---|---|
| 6,859,514 | B2 | 2/2005 | Hoffman |
| 2004/0065465 | A1 | 4/2004 | Chappo et al. |
| 2004/0065839 | A1 | 4/2004 | Elgali |
| 2007/0206721 | A1* | 9/2007 | Tkaczyk .............. A61B 6/032 378/19 |
| 2008/0068815 | A1 | 3/2008 | Astley et al. |
| 2011/0095191 | A1* | 4/2011 | Takihi .................. G01N 23/04 250/366 |
| 2011/0305315 | A1* | 12/2011 | Park .................... A61B 6/0407 378/62 |
| 2012/0069956 | A1 | 3/2012 | Guery et al. |
| 2012/0183119 | A1* | 7/2012 | Ikhlef .................. A61B 6/035 378/19 |
| 2012/0230003 | A1* | 9/2012 | Stevenson ............ A61N 1/375 361/816 |
| 2014/0064443 | A1* | 3/2014 | Kato .................... A61B 6/4429 378/19 |
| 2014/0369462 | A1* | 12/2014 | Lacey .................. A61B 6/03 378/19 |

FOREIGN PATENT DOCUMENTS

| | | |
|---|---|---|
| CN | 101410983 A | 4/2009 |
| CN | 102681020 A | 9/2012 |
| CN | 103083034 A | 5/2013 |
| CN | 103549967 A | 2/2014 |

* cited by examiner

DETECTOR SYSTEM OF CT SCANNER

CROSS-REFERENCE TO RELATED APPLICATIONS

The present application claims priority to Chinese Patent Application No. 201410765565.9, filed on Dec. 12, 2014, and Chinese Patent Application No. 201510889368.2, filed on Dec. 4, 2015, the entire contents of which are hereby incorporated by reference for all purposes.

BACKGROUND

A detector system may be an important component for achieving photoelectric conversion in a computed tomography (CT) scanner, and may usually be composed of a plurality of independent detectors arranged in a rectangular pattern along the X-axis direction and the Z-axis direction of the CT scanner.

With the performance improvement of the CT scanner, the detector system gets larger and larger. When a single detector is to be embedded in the detector system, consideration for convenience of installation, removal and replacement may be required, and thermal performance and radiation-proof performance should also be considered.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS' latest successful developments, such as the 128 Multi-Slice CT Scanner System, Superconducting MRI, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

Features of the present disclosure are illustrated by way of example and are not limited in the following figure(s), in which like numerals indicate like elements, in which.

DETAILED DESCRIPTION

For simplicity and illustrative purposes, the present disclosure may be described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

To make description more accurate, an X-Y-Z three-dimensional coordinate system of a detector system of a CT scanner is briefly described first. Please refer to FIG. 6, which is a diagram showing a relationship between the detector system and the three-dimensional coordinate system. The detector system may comprise a backplane 610, a plurality of detector modules 620 and a casing 630 for supporting and connecting electrical components including the detector modules 620 and the backplane 610. The Z direction may be a direction perpendicular to a plane where a backplane 610 located, and may usually be a layer direction of the detector system; the Y direction may be a vertical direction; and the X direction may be perpendicular to the Y-Z plane.

In the present disclosure, first, a plurality of detectors may be spliced as a row along a first direction to constitute a detector module; and then a plurality of detector modules may be spliced along a second direction to constitute a rectangle-shaped detector system. For a CT scanner, a detector system may usually be a rectangle in the X-Z coordinate system. Therefore, the X-direction may be set as the first direction while the Z-direction may be set as the second direction; or vice versa, the X-direction may be set as the second direction while the Z-direction may be set as the first direction.

FIG. 1 to FIG. 5 illustrates a detector module according to an example of the present disclosure. In this example, four detectors constituting a detector module is shown. In practice, based on the following structure, a number of the detectors of the detector module may be increased or decreased in accordance with demands.

Figure 1:
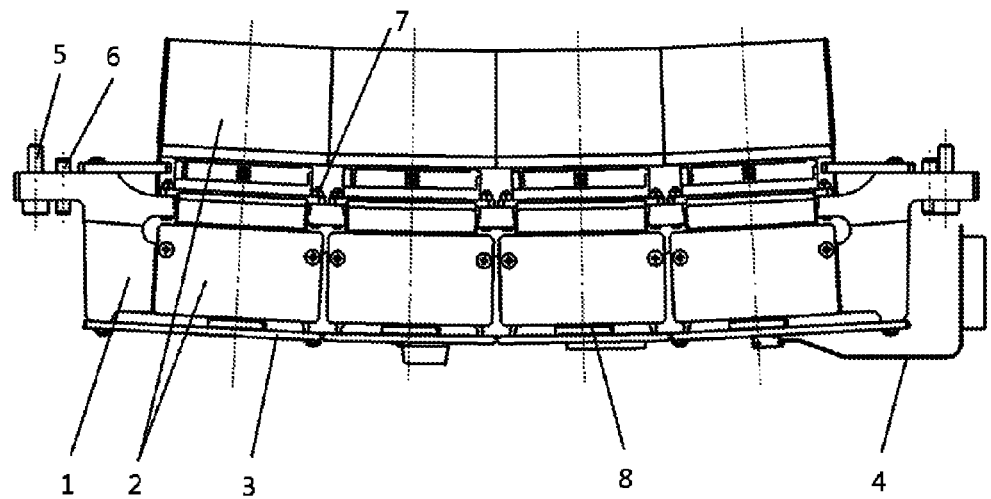
FIG. 1 is a side view of a detector module according to an example of the present disclosure.

FIG. 1 is a side view of a detector module according to an example of the present disclosure, wherein a detector module may include a supporting frame 1. The material of a supporting frame 1 may be a metal having a high thermal conductivity, such as an aluminum alloy or a zinc alloy, etc., in order to ensure cooling of the detector module. A supporting frame 1 may be manufactured through metal casting technology or other processing machining technology for supporting other components of a detector module, and may be a basic component for constituting a detector module.

Two ends of a supporting frame 1 may include a connecting structure for connecting a detector module with a casing of a detector system. A fixing screw 5 of a connecting structure may be used to fix a detector module to a casing of a detector system; and a pin 6 may be used to ensure a position accuracy of a detector module during the process of fixing the detector module. A lower portion of a supporting frame 1 may be a shape of metal heat sink, and an air circulation channel may be formed along an extending direction of a detector module. The specific structure of a supporting frame 1 may be seen by referring to FIG. 4 and related description.

As shown in FIG. 1, a detector module may include four independent detectors 2. Each of the detector 2 may be a component for converting an X-ray beam within the CT scanner into an electrical signal (a digital signal), and may be a main body portion of a detector module. The detector 2 may be mounted on a supporting frame 1; that is, after the detector 2 and the supporting frame 1 may be accurately positioned through a positioning tooling, a fixing screw 7 may be used to fix a detector 2 to a supporting frame 1. The specific structure of a detector 2 may be seen by referring to FIG. 2-FIG. 3 and related description.

In an example, a supporting frame 1 may have a targeted structural design based on specific circumstances. As a result, after a detector module may be mounted in the CT scanner, symmetrical centerlines of each of the detectors 2 in a detector module may be extended to intersect at the focus of the X-ray tube of the CT scanner, which may ensure that each of the detectors 2 in a detector module has a better consistency along the extending direction of the detector module.

An interface board 3 may be disposed in an outer side of a supporting frame 1 away from a focus of the X-ray tube. The interface board 3 may be electrically connected to the detectors 2 through a connector 8, for providing a control signal and a power supply to the detectors 2, and for transmitting a digital signal outputted by the detectors 2 to a backplane of the detector system through an output line 4. A backplane may be used for providing power and the control signal to the detector module, and for transmitting signals outputted by the detector module to a circuit board of a signal transmission system for the detector system.

Figure 5:
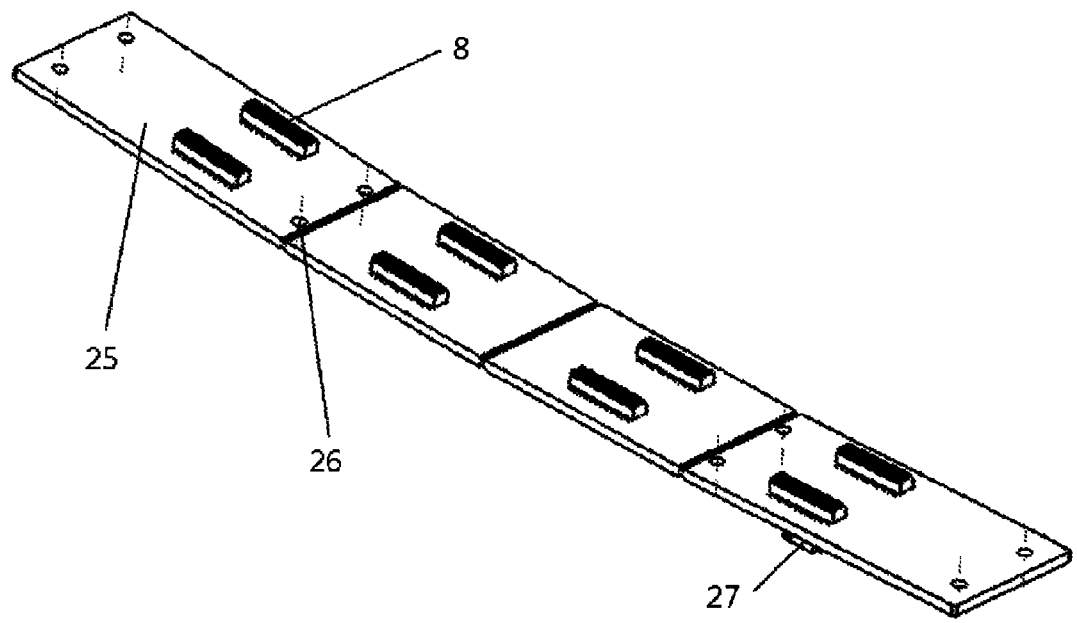
FIG. 5 is a 3D architecture diagram of an interface board of the detector module according to an example of the present disclosure.

The specific structure of an interface board 3 may be seen by referring to FIG. 5 and its related description.

Figure 2:
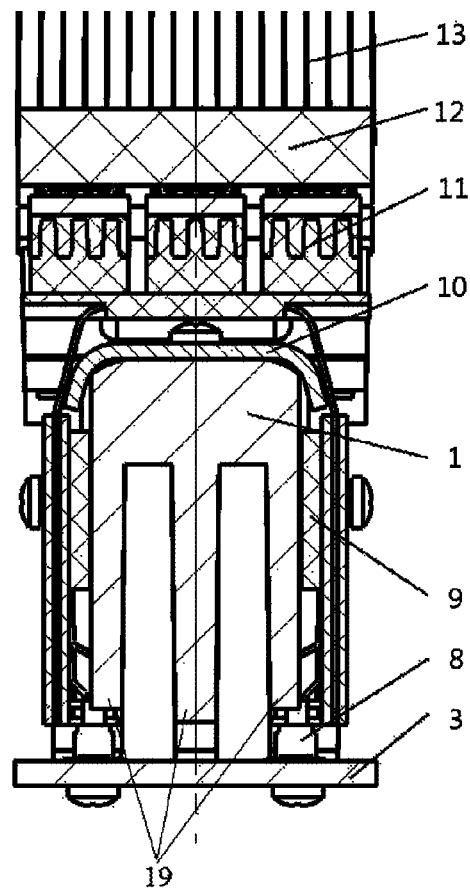
FIG. 2 is a cross-sectional view of a detector module according to an example of the present disclosure.

FIG. 2 is a cross-sectional view of a detector module according to an example of the present disclosure. A detector 2 may mainly include a raster collimator 13, a photodiode 12, an analog signal connector 11 and an analog-to-digital conversion Integrated Circuit (hereinafter referred as "IC") 9.

The raster collimator 13 may be used for absorbing an X-ray beam scattered by the CT scanner, and the raster collimator 13 may be bonded to the photodiode 12 through anti-X-ray radiation glue.

The photodiode 12 may be a core component for photoelectric conversion, and may be used for converting an X-ray beam into a visible light beam and for converting a visible light beam into an analog electrical signal. The photodiode 12 may be typically consisted of, from top to bottom, a scintillator array, a photosensitive silicon chip, a substrate, and a connecting assembly.

The analog signal connector 11 may be used for transmitting the analog electrical signal generated by a photodiode 12 to an analog-to-digital conversion IC 9.

An analog signal connector 11 may comprise two removable parts, wherein one removable part may be connected to the photodiode 12 and the other one removable part may be connected to the analog-to-digital conversion IC 9, and thus a photodiode 12 may be electrically connected to the analog-to-digital conversion IC 9.

Meanwhile, the part for connecting an analog signal connector 11 to a photodiode 12 may also be used as a fixing member of the photodiode 12, and thus a photodiode 12 may be achieved to be detachable from or fixed to an analog signal connector 11. In another example, in order to more reliably fix the photodiode 12, two parts of an analog signal connector 11 may be bonded and fixed through anti-X-ray radiation glue after the detector module may be assembled and adjusted.

The analog-to-digital conversion IC 9 may also be an important component for photoelectric conversion, and may be used to convert an analog electrical signal into a digital signal. In this example, by using a photodiode 12 and an analog-to-digital conversion IC 9, a series of signal conversions, such as X-ray beam→a visible light beam→an analog electrical signal→a digital signal, may be achieved in order to implement core functions of the detector 2.

It should be understood that, an analog-to-digital conversion IC 9 may be the major heat source of the detector 2, so it may be bonded to a supporting frame 1, and a bonding surface between the analog-to-digital conversion IC 9 and a supporting frame 1 may be coated with thermal grease for further improving thermal effects.

A shielding plate 10 may be disposed between the analog-to-digital conversion IC 9 and an analog signal connector 11, for shielding the analog-to-digital conversion IC 9 and other components from an X-ray beam emitted by the X-ray tube of the CT scanner. In order to ensure a shielding effect, in this example, a shielding plate 10 may be designed as having an "n"-shaped curved cross-section and two drooping sides of an "n"-shaped curved cross-section may be of a splayed shape. This structure may provide a better shielding effect than a flat shape structure along a straight radiation path from the focus of the X-ray tube of the CT scanner to an upper side of the analog-to-digital conversion IC 9. A shielding plate 10 may be manufactured by adopting tungsten, lead, molybdenum or similar alloy metal materials with high X-ray attenuation.

As shown in FIG. 2, an interface board 3 and an analog-to-digital conversion IC 9 made up of the rigid-flex printed circuit board (PCB), may constitute a ring enclosing a supporting frame 1, such that a cavity may be formed between an internal heat sink 19 of a supporting frame 1 and an interface board 3 and acts as an air circulation channel. Therefore, when the detector module may be operating, a flowing air with a certain pressure may be applied in an air circulation channel for cooling the detector module.

Figure 3:
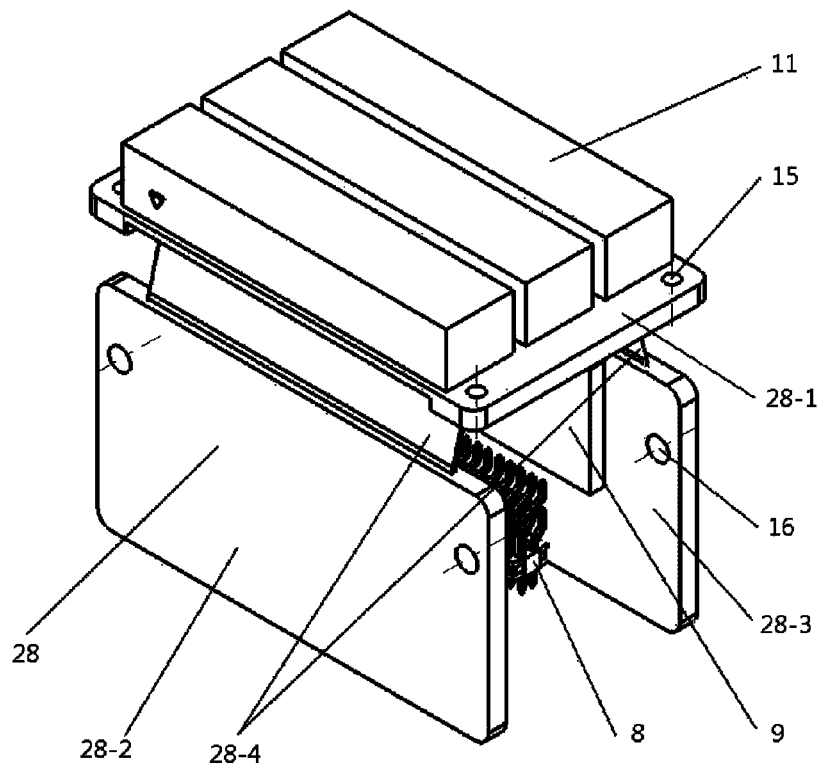
FIG. 3 is a 3D architecture diagram of an analog-to-digital conversion circuit board area of the detector module according to an example of the present disclosure.

FIG. 3 is a 3D architecture diagram of an analog-to-digital conversion circuit board area of a detector module according to an example of the present disclosure. An analog-to-digital conversion circuit board area may mainly include an analog signal connector 11, an analog-to-digital conversion IC 9, a connector 8 and a rigid-flex printed circuit board (PCB) 28. A rigid-flex PCB 28 may include a first fixing portion 28-1 for fixing the analog signal connector 11, a second fixing portion (a left fixing portion) 28-2 and a third fixing portion (a right fixing portion) 28-3 for fixing the analog-to-digital conversion IC 9, and a flexible connecting belt 28-4 for connecting the first fixing portion 28-1, the second fixing portion 28-2, and the third fixing portion 28-3. A first fixing portion 28-1 of an analog signal connector 11 may include four fixing holes 15 for connecting the detectors 2 to a supporting frame 1. A left fixing portion 28-2 of the analog-to-digital conversion IC 9 and a right fixing portion 28-3 of an analog-to-digital conversion IC 9 may include two fixing holes 16, respectively. Fixing holes 16 may be used to connect a left fixing portion 28-2 of an analog-to-digital conversion IC 9 and a right fixing portion 28-3 of an analog-to-digital conversion IC 9 to a sidewall of a supporting frame 1, and bond an analog-to-digital conversion IC 9 and a metal heat sink of a supporting frame 1 for cooling. In another example, in order to achieve better cooling effects, thermal grease may be coated between the analog-to-digital conversion IC 9 and the metal heat sink of the supporting frame 1.

Figure 4:
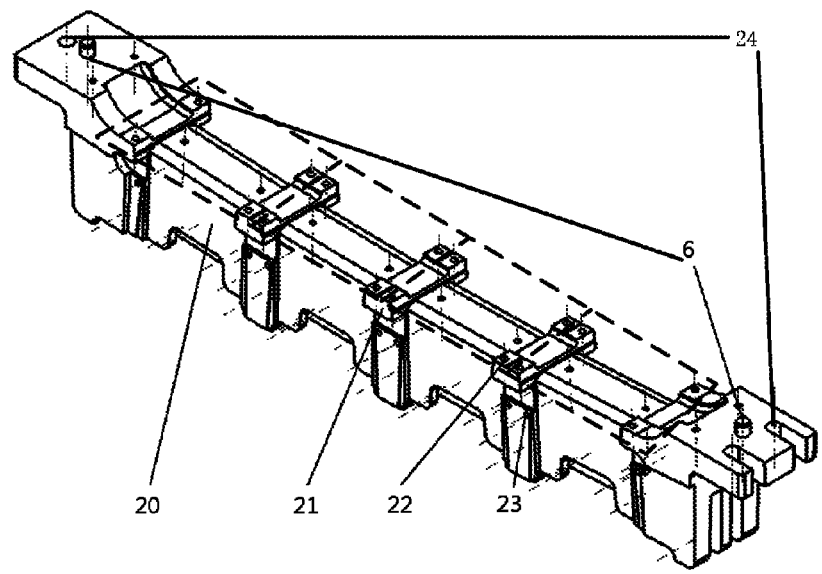
FIG. 4 is a 3D architecture diagram of a supporting frame of the detector module according to an example of the present disclosure.

FIG. 4 is a 3D architecture diagram of a supporting frame 1 of a detector module according to an example of the present disclosure.

A first fixing hole 24 may be configured in an end of a supporting frame 1 for fixing the supporting frame 1 to the casing of a detector system.

When mounting a detector 2 to a supporting frame 1, an analog-to-digital conversion IC 9 may contact the supporting frame 1 with a large area. In order to firmly mount a detector 2 to a supporting frame 1, a second fixing hole 22 and a third fixing hole 23 corresponding to the detector 2 (namely the analog-to-digital conversion IC of the detector 2) may be disposed on the supporting frame 1. As shown in FIG. 3 together with FIG. 4, a third fixing hole 23 may correspond to the fixing holes of a left fixing portion 28-2 and a right fixing portion 28-3 of an analog-to-digital conversion IC 9, and a second fixing hole 22 may correspond to a fixing hole of a first fixing portion 28-1 of the analog signal connector 11 in an analog-to-digital conversion circuit board. The sidewall 20 of a supporting frame 1 may also match an analog-to-digital conversion IC 9, and a sidewall 20 may be processed to ensure the matching accuracy of an analog-to-digital conversion IC 9.

A convex cantilever structure 21 may be disposed at a position of the supporting frame 1 which may correspond to a first fixing portion 28-1 of the analog signal connector 11, such as an area circled within dotted lines shown in FIG. 4. A number of convex cantilever structures 21 in the supporting frame 1 may be equal to a number of detectors 2 in the detector module. For example, if a detector module is spliced by four detectors 2, as shown in FIG. 4, and thus four substantially convex cantilever structures 21 may be required. Each convex cantilever structure 21 may comprise four support points for constituting a flat plane, hereinafter referred to as a top plane of the convex cantilever structure 21. There may be an induced angle between each top plane of a convex cantilever structure 21, wherein an induced angle makes symmetrical centerlines of each of the detectors 2 in a detector module and may be extended to intersect in the focus of an X-ray tube of the CT scanner after a detector module may be assembled. Therefore, it ensures that each of the detectors 2 of a detector module may have a better consistency along an extending direction of the detector module. A space for accommodating a shielding plate 10 may be reserved in the distance between adjacent convex cantilever structures 21 of the supporting frame 1.

In this example, the contact area between the convex cantilever structures 21 and a first fixing portion 28-1 of an analog signal connector 11 may be smaller, which may reduce heat transferred from a supporting frame 1 to a first fixing portion 28-1 of the analog signal connector 11, and may reduce heat transfer from an analog signal connector 11 to a photodiode 12 and a raster collimator 13. As a result, the whole detector module may have an improved thermal stability.

FIG. 5 is a 3D architecture diagram of an interface board 3 of a detector module according to an example of the present disclosure. An interface board 3 may mainly include a connector 8, a backplane connector 27, a substrate 25, and related electrical components disposed on the substrate 25. An interface board 3 may be mounted to a supporting frame 1 through a connecting hole. The substrate 25 of the interface board 3 may consist of a plurality of rigid-flex PCBs, and adjacent rigid-flex PCBs may be connected through flexible belts 26. In an example, the flexible belt 26 may be appropriately extended to a length capable of being bent into an Ω shape, such that each rigid portion may be aligned with a corresponding detector module during installation process. Therefore, the substrate 25 may match the curvature of a supporting frame 1 through the bending of a flexible belt 26 in order to accurately connect the detectors 2 aligned in a fan shape to the connectors 8.

In another example, an interface board 3 may also be divided into a plurality of sub-boards independently corresponding to their own detectors 2, respectively (not shown in FIG. 5).

If a detector module is manufactured based on the above structure, it may meet requirements of thermal performance and radiation-proof performance of a large-scale detector system. Furthermore, if a plurality of detector modules is spliced as a detector system, it may meet convenience requirements of installation, removal and replacement of a large-scale detector system.

Figure 6:
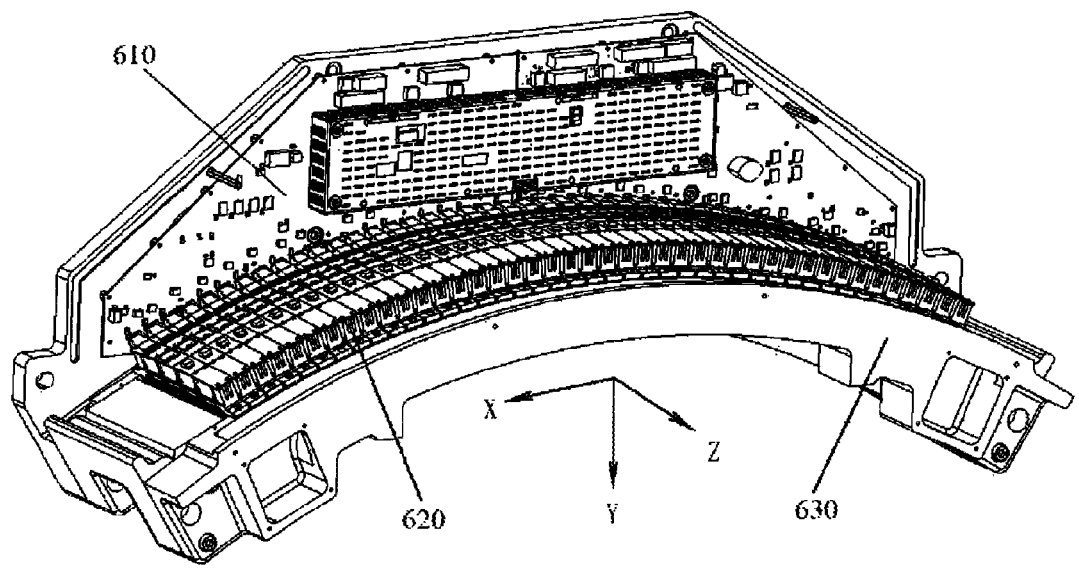
FIG. 6 is a 3D architecture diagram of the detector system according to an example of the present disclosure.

FIG. 6 is a 3D architecture diagram of the detector system according to an example of the present disclosure. A plurality of detector modules 620 mentioned in the examples of the present disclosure may be spliced as a rectangle-shaped detector system. A detector system may be manufactured by the abovementioned detector modules, and thus it includes all features of the detector modules.

The above may be preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product may be stored in a storage medium and may comprise a plurality of instructions for making a processor to implement the methods recited in the examples of the present disclosure.

The figures are only illustrations of an example, wherein the units or procedure shown in the figures may not be necessarily essential for implementing the present disclosure. Those skilled in the art will understand that the units in the device in the example may be arranged in the device in the examples as described, or may be alternatively located in one or more devices different from that in the examples. The units in the examples described may be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations may be within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A detector system of a CT scanner, the detector system comprising a plurality of detector modules, each of the detector modules comprising:
   a supporting frame, connected to a casing of the detector system of the CT scanner;
   two or more detectors, mounted on the supporting frame, for converting an X-ray beam within the CT scanner into an electrical signal, wherein each of the detectors comprises:
      a collimator, for absorbing the X-ray beam scattered by the CT scanner;
      a photodiode, for converting the X-ray beam into a visible light beam and for converting the visible light beam into an analog electrical signal, wherein the collimator is bonded to the photodiode;
      an analog-to-digital conversion integrated circuit (IC), for converting the analog electrical signal into a digital signal; and
      an analog signal connector, for transmitting the analog electrical signal generated by the photodiode to the analog-to-digital conversion IC;
   an interface board, disposed in an outer side of the supporting frame away from a focus of an X-ray tube, and electrically connected to the detectors through a connector, for providing a control signal and a power supply to the detectors, and for transmitting a digital signal outputted by the detector to a backplane of the detector system through an output line; and
   a shielding plate, disposed between the analog-to-digital conversion IC and the analog signal connector, for shielding an X-ray beam emitted by the X-ray tube of the CT scanner, and designed as having an n-shaped curved cross-section and two drooping sides of the n-shaped curved cross-section being of a splayed shape.

2. The detector system of claim 1, wherein the analog-to-digital conversion IC is bonded to the supporting frame; and
   a bonding surface between the analog-to-digital conversion IC and the supporting frame is coated with a thermal grease.

3. The detector system of claim 1, wherein the analog signal connector comprises two removable parts;
   one of the removable parts is connected to the photodiode and is used as a fixing member of the photodiode; and
   the other one of the removable parts is connected to the analog-to-digital conversion IC, and thus the photodiode is achieved to be detachable from or fixed to the analog signal connector.

4. The detector system of claim 1, wherein each of the detectors further consists of a rigid-flex printed circuit board (PCB), and the rigid-flex PCB comprises:
   a first fixing portion, for fixing the analog signal connector;
   a second fixing portion and a third fixing portion, for fixing the analog-to-digital conversion IC; and
   a flexible connecting belt, for connecting the first fixing portion, the second fixing portion, and the third fixing portion.

5. The detector system of claim 4, wherein the rigid-flex PCB and the interface board constitute a ring enclosing the supporting frame.

6. The detector system of claim 1, wherein the supporting frame further comprises:
   first fixing holes, configured in an end of the supporting frame, for fixing the supporting frame to the casing of the detector system; and
   second fixing holes and third fixing holes, for mounting each of the detectors.

7. The detector system of claim 1, wherein the supporting frame further comprises:
   convex cantilever structures, respectively disposed at a position of the support frame for mounting each of the detectors;
   wherein a number of the convex cantilever structures in the supporting frame is equal to a number of the detectors in the detector module; and
   a top edge of each of the convex cantilever structures is planar, and there is an induced angle between each of the top edges of the convex cantilever structures.

8. The detector system of claim 7, wherein the induced angle makes symmetrical centerlines of each of the detectors in the detector module be extended to intersect at the focus of the X-ray tube of the CT scanner.

9. The detector system of claim 1, wherein a material of the supporting frame is a metal, and the supporting frame is manufactured through a metal casting and machining process.

10. The detector system of claim 9, wherein a lower portion of the supporting frame is of a shape of a metal heat sink.

11. The detector system of claim 5, wherein an air circulation groove is formed between the interface board and an internal heat sink of the supporting frame.

12. The detector system of claim 1, wherein the interface board consists of a plurality of rigid-flex printed circuit boards (PCBs), and adjacent rigid-flex PCBs are connected through flexible belts.

* * * * *